(12) United States Patent
Josephson

(10) Patent No.: US 6,679,897 B2
(45) Date of Patent: Jan. 20, 2004

(54) ADENOID CURETTE

(76) Inventor: Gary D. Josephson, 915 Yacht Harbor Ct., Jacksonville, FL (US) 32225

( * ) Notice: Subject to any disclaimer, the term of this patent is extended or adjusted under 35 U.S.C. 154(b) by 109 days.

(21) Appl. No.: 09/930,588

(22) Filed: Aug. 14, 2001

(65) Prior Publication Data

US 2003/0036769 A1 Feb. 20, 2003

(51) Int. Cl.⁷ .............................. A61D 1/02; A61B 17/04
(52) U.S. Cl. ..................... 606/160; 606/170; 600/570
(58) Field of Search ..................... 606/170, 1, 160, 606/161, 162, 166, 176; 600/562, 592, 570, 571

(56) References Cited

U.S. PATENT DOCUMENTS

| | | | | |
|---|---|---|---|---|
| 651,395 A | * | 6/1900 | Stapp | 606/160 |
| 654,763 A | * | 7/1900 | Russell | 606/160 |
| 3,886,943 A | * | 6/1975 | Skiff et al. | |
| 4,259,069 A | * | 3/1981 | Lustig | 433/144 |
| 4,932,957 A | * | 6/1990 | Zwick | 606/160 |
| 5,090,907 A | * | 2/1992 | Hewitt et al. | 433/144 |
| 5,217,024 A | * | 6/1993 | Dorsey et al. | 600/571 |
| 5,250,061 A | * | 10/1993 | Michelson | 606/160 |
| 5,348,023 A | * | 9/1994 | McLucas | 600/570 |
| 5,586,989 A | * | 12/1996 | Bray, Jr. | 606/160 |
| 5,902,314 A | * | 5/1999 | Koch | 606/160 |
| 6,018,094 A | * | 1/2000 | Fox | 606/191 |
| 6,447,525 B2 | * | 9/2002 | Follmer et al. | 606/159 |

* cited by examiner

*Primary Examiner*—Gary Jackson
(74) *Attorney, Agent, or Firm*—Charles E. Baxley

(57) ABSTRACT

An adenoid curette that includes a shank, a handle, and a cutting head. The shank has a pin, male threads, and a collar. The cutting head is a loop that is continuous and has a groove, a slot, and a neck. The shank is placed in the groove and in the neck, and the pin is positioned in the slot. The collar is threaded onto the male threads, captures the neck during threading, and abuts against the cutting head during threading so as to force the pin further into the slot until the collar can no longer rotate indicating that the pin is fully seated in the slot and thereby causing the cutting head to be captured between the pin and the collar and thereby interchangeably retaining the cutting head on the shank.

23 Claims, 7 Drawing Sheets

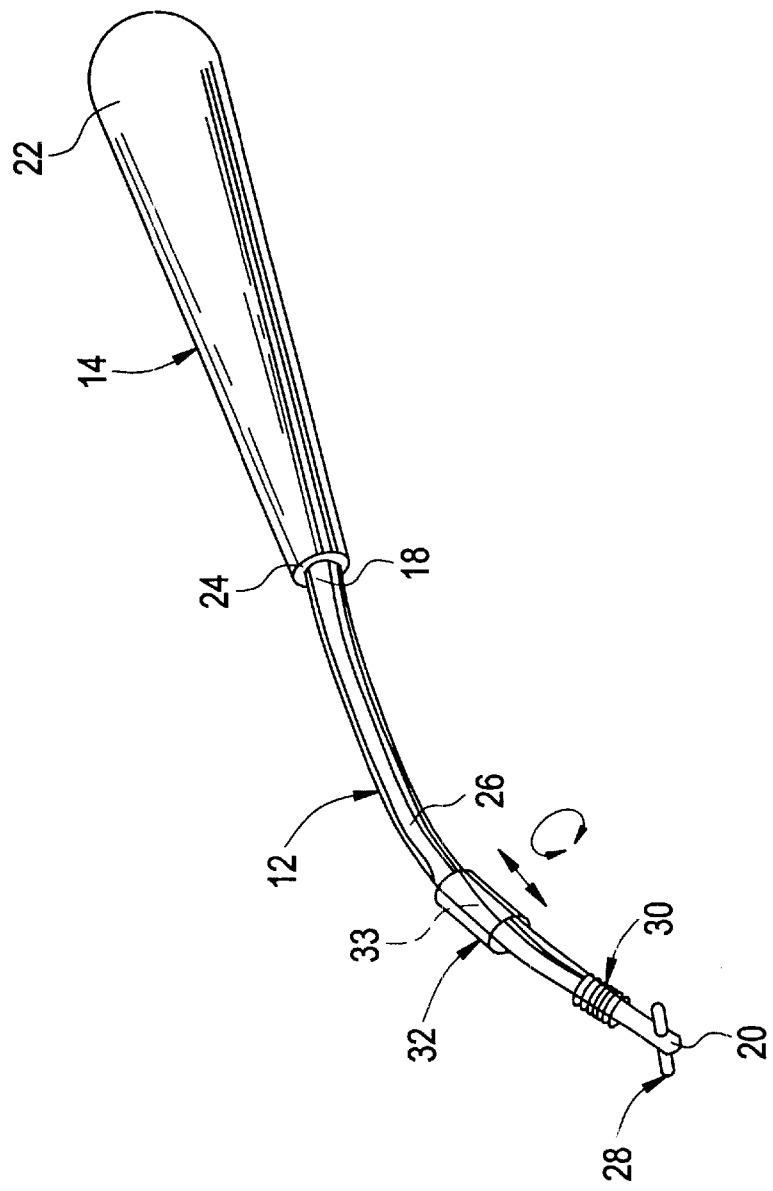

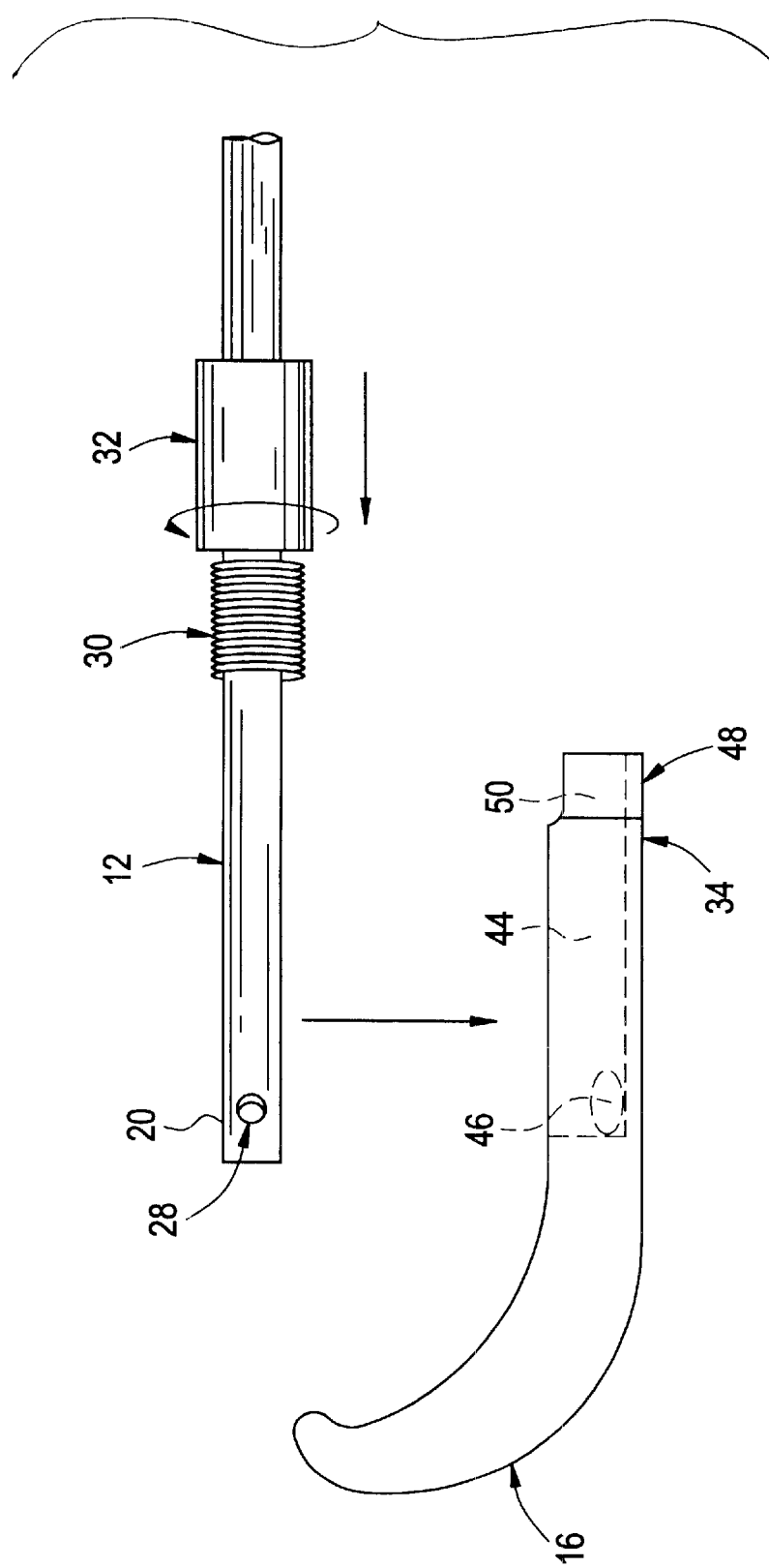

STEP 6 b

ABUT THE COLLAR (32) AGAINST THE REARWARDMOST TRANSVERSE PORTION (34) OF THE CUTTING HEAD (16) DURING THREADING SO AS TO DRAW THE PIN (28) FURTHER INTO THE SLOT (46) UNTIL THE COLLAR (32) CAN NO LONGER ROTATE INDICATING THAT THE PIN (28) IS FULLY SEATED IN THE SLOT (46) AND THEREBY CAUSING THE REARWARDMOST PORTION (34) OF THE CUTTING HEAD (16) TO BE CAPTURED BETWEEN THE PIN (28) AND THE COLLAR (32) AND THEREBY INTERCHANGEABLY RETAINING THE CUTTING HEAD (16) ON THE SHANK (16)

END

FIG. 5C

ADENOID CURETTE

BACKGROUND OF THE INVENTION

1. Field of the Invention

The present invention relates to the class of surgery. More particularly, the present invention relates to the subclass of curettes.

2. Description of the Prior Art

Excessive growth of the pharyngeal tonsil or adenoid produces a condition commonly found in children. The enlargement may block the nasal passages or eustachian tube and produce disturbances in breathing and hearing. If severe, the child may assume a characteristic vacant, stupid expression accompanied by mouth breathing. The presence of these growths may handicap the child in his physical and mental development.

Fortunately, surgical removal is relatively simple with the use of an adenoid curette, which is a surgical instrument that includes a handle, a shank, and a cutting head. The shank is either straight or curved and the cutting head is of varying sizes to accommodate for different patient characteristics.

Heretofore, adenoid curettes were fabricated from solid one-piece material, a typical manufacturer being STORZ. The use of one-piece adenoid curettes require the physical or medical facility to obtain a large number of separate instruments, often at great expense, for accommodating for the different sized cutting heads. Also, sterilization and resharpening of the cutting head is necessary to maintain a sterile and consistently sharp edge during use, which is critical since a sharp precise removal of the adenoids is required.

Thus, there is a need for an adenoid curette whose cutting head is interchangeable so as to accommodate for different patient characteristics and thereby eliminate a need for a physical or medical facility to obtain a large number of separate instruments for accommodating for the different sized cutting heads and whose cutting head is disposable so as to eliminate a need for sterilization and resharpening thereof to maintain a sterile and consistently sharp edge during use.

Numerous innovations for curettes and bladed surgical instruments have been provided in the prior art that will be described. Even though these innovations may be suitable for the specific individual purposes to which they address, however, they differ from the present invention.

FOR EXAMPLE, U.S. Pat. No. 3,502,082 to Chatfield teaches a surgical instrument comprising a curette having a disposable single or double-edged stainless steel razor band loop blade for cutting and cleaning out cavities in tissue and as a microtome, knife, eraser, and abrader.

ANOTHER EXAMPLE, U.S. Pat. No. 4,798,000 to Bedner et al. teaches a detachable cutting blade assembly that includes an elongated handle having a rear end and a front end on which a cutting blade can be detachably supported and a blade-locking member, in the form of a wall, is secured to the top surface of the front end of the handle. A portion of the wall of the blade-locking member has lateral lips which give the wall a T-shaped cross section and this provides securement for a cutting blade. The lips of the blade-locking member are aligned with a hole in the handle and this permits the entire handle to be made with a two-part mold in a relatively inexpensive molding process.

STILL ANOTHER EXAMPLE, U.S. Pat. No. 4,985,035 to Torre teaches a surgical instrument that provides a handle for removably attaching blades having different sizes and different purposes for performing different surgical procedures.

YET ANOTHER EXAMPLE, U.S. Pat. No. 5,250,061 to Michelson teaches an improved ring curette for the removal of pathological body tissues.

STILL YET ANOTHER EXAMPLE, U.S. Pat. No. 5,586,989 to Bray, Jr. teaches a curette including a cylindrical handle, having a longitudinal axis, and a shaft, having a longitudinal axis. The shaft is attached to the cylindrical handle at a first end of the shaft, such that the longitudinal axis of the shaft is parallel to, but not collinear with, the longitudinal axis of the cylindrical handle. A tip is included in a second end of the shaft.

YET STILL ANOTHER EXAMPLE, U.S. Pat. No. 5,827,307 to Tipton teaches a disposable hemostatic curette that includes a handle, at least one scraping implement, and a crushable applicator. The handle has a first end, a second end, and a length. The cross section and length of the handle are sized to facilitate easy manipulation with a thumb and forefinger. The first end of the handle is tapered to a smaller diameter which is connected to a scraping implement. The scraping implement is preferably round in shape with a shallow bore. A scraping edge of the scraping implement is a sharp edge which is formed from the inner wall of the shallow bore and a tapering outer wall of the scraping implement. A deep bore is formed in the second end of the handle, and is sized to firmly receive the outside diameter of a crushable applicator. The crushable applicator includes a transparent flexible housing, an applicator swab, and a crushable ampule containing a hemostatic solution. At least one crush window is disposed at the second end of the handle. The crush window is an opening through the second end of the handle to the deep bore disposed in thereof. The crush window is sized to allow a thumb and forefinger to break the crushable ampule located inside the crushable applicator which wets the applicator swab.

STILL YET ANOTHER EXAMPLE, U.S. Pat. No. 5,836,958 to Ralph teaches a curette having a variably angled handle that includes a curette member which has a disc shaped end. The disc shaped end has a hole through its center and a series of discrete angular graduations on its edge. The disc shaped end is retained via a pin in a recess in the proximal end of a handle. The handle includes an axial bore through which a shaft extends into selective contact with the graduations on the disc shaped end of the curette member. The curette may be angularly positioned relative to the handle if the shaft is selectively disengaged from its contact with the graduations of the disc shaped end of the curette member, but not once the shaft has engaged the graduations. The shaft may be selectively engaged by a variety of different ways, including spring biasing, threading and having a selectively extendable handle.

YET STILL ANOTHER EXAMPLE, U.S. Pat. No. 6,074,405 to Koch teaches a medical instrument that is adapted to remove obstructions from ear canals, nostrils, and endotracheal tube airways. It includes an elongated handle with an elongated hollow tube connected to the front end thereof and an elongated flexible wire extending from the front end of the tube. The front end of the wire is curved to form a scoop for removing obstructions from a lumen. In one embodiment, the wire and tube are removable as a replaceable unit from the front end of the handle. In another embodiment, the handle has a central cavity therein communicating with the cavity in the tube and through both of which the wire extends. The wire is connected to a spring which extends out of the handle. The spring biases the wire into the tube. When the wire is manually depressed, the front end of the wire extends out of the tube and curves into the desired scoop configuration. The instrument can include a light which is switched on when the wire extends out of the tube and which is used to light the lumen. In another embodiment, the front end of the wire forms a loop which goes back into the tube, which is flexible, the loop being extendable from the tube by spring biasing. In a further embodiment, one end of the loop is secured to the exterior of the tube and the loop is shielded by a removable cap.

It is apparent that numerous innovations for curettes and bladed surgical instruments have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an adenoid curette that avoids the disadvantages of the prior art.

ANOTHER OBJECT of the present invention is to provide an adenoid curette that is simple to use.

STILL ANOTHER OBJECT of the present invention is to provide an adenoid curette whose cutting head is disposable by being quickly attached to, and removed from, the shank of the instrument so that a sharp and sterilized blade is available at all times.

YET ANOTHER OBJECT of the present invention is to provide an adenoid curette whose cutting head is interchangeable by being quickly attached to, and removed from, the shank of the instrument so that different sized cutting heads are available at all times for accommodating various characteristics of a patient.

BRIEFLY STATED, STILL YET ANOTHER OBJECT of the present invention is to provide an adenoid curette that includes a shank, a handle, and a cutting head. The shank has a pin, male threads, and a collar. The cutting head is a loop that is continuous and has a groove, a slot, and a neck. The shank is placed in the groove and in the neck, and the pin is positioned in the slot. The collar is threaded onto the male threads, captures the neck during threading, and abuts against the cutting head during threading so as to force the pin further into the slot until the collar can no longer rotate indicating that the pin is fully seated in the slot and thereby causing the cutting head to be captured between the pin and the collar and thereby interchangeably retaining the cutting head on the shank so as to allow different cutting heads to be used for accommodating various characteristics of a patient and so as to allow the cutting head to be disposable and eliminate a need for sterilization and resharpening thereof.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 2A is a diagrammatic perspective view of the curved shank and the handle of the present invention;

FIG. 4 is an exploded diagrammatic side elevational view taken generally in the direction of ARROW 4 in FIG. 1; and FIGS. 5A–5C are a flow chart of the method of interchangeably retaining the cutting head of the present invention shown in FIG. 3 on the shank of the present invention shown in FIG. 2.

Figure 1:
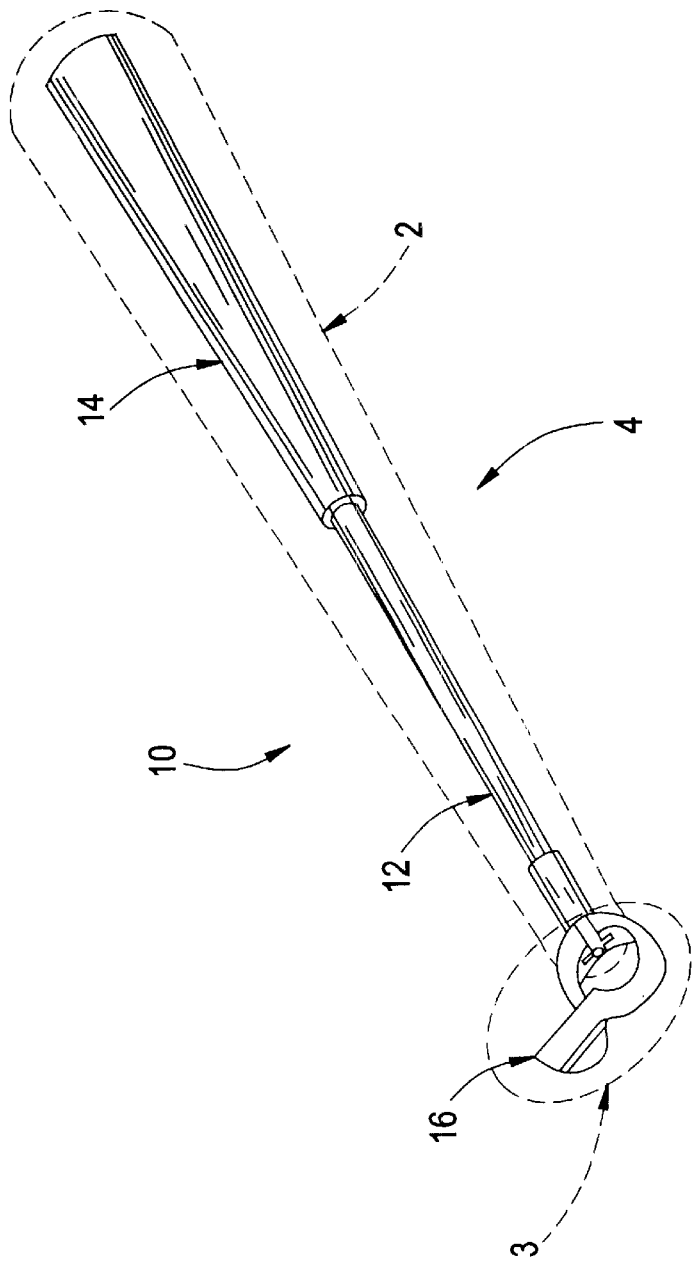
FIG. 1 is a diagrammatic perspective view of the adenoid curette of the present invention.

LIST OF REFERENCE NUMERALS UTILIZED IN THE DRAWING 10 adenoid curette of present invention
12 shank
14 handle
16 cutting head
18 proximal end of shank 12
20 distal end of shank 12
22 proximal end of handle 14
24 distal end of handle 14
26 intermediate point of shank 12
28 pin on shank 12
30 male threads on shank 12
32 collar on shank 12
33 female threads contained in collar 32 of shank 12
34 rearwardmost transverse portion of cutting head 16
36 pair of ends of rearwardmost transverse portion 34 of cutting head 16
38 midpoint of rearwardmost transverse portion 34 of cutting head 16
40 forwardmost surface of rearwardmost transverse portion 34 of cutting head 16
42 rearwardmost surface of rearwardmost transverse portion 34 of cutting head 16
44 groove extending perpendicularly in rearwardmost transverse portion 34 of cutting head 16
46 slot extending in forwardmost surface 40 of rearwardmost transverse portion 34 of cutting head 16
48 neck of cutting head 16
50 split extending longitudinally and completely along neck 48 of cutting head 16
52 pair of legs of cutting head 16
54 pair of ends of pair of legs 52 of cutting head 16, respectively
56 forwardmost transverse portion of cutting head 16
58 rearwardmost surface of forwardmost transverse portion 56 of cutting head 16
60 blade of cutting head 16

DETAILED DESCRIPTION OF THE PREFERRED EMBODIMENT

Referring now to the figures, in which like numerals indicate like parts, and particularly to FIG. 1, which is a diagrammatic perspective view of the adenoid curette of the present invention, the adenoid curette of the present invention is shown generally at 10.

The adenoid curette 10 includes a shank 12, a handle 14 that extends coaxially from the shank 12, and a cutting head 16 that is interchangeably retained on the shank 12 so as to allow different cutting heads 16 to be used for accommodating various characteristics of a patient and so as to allow the cutting head 16 to be disposable and eliminate a need for sterilization and resharpening thereof.

Figure 2:
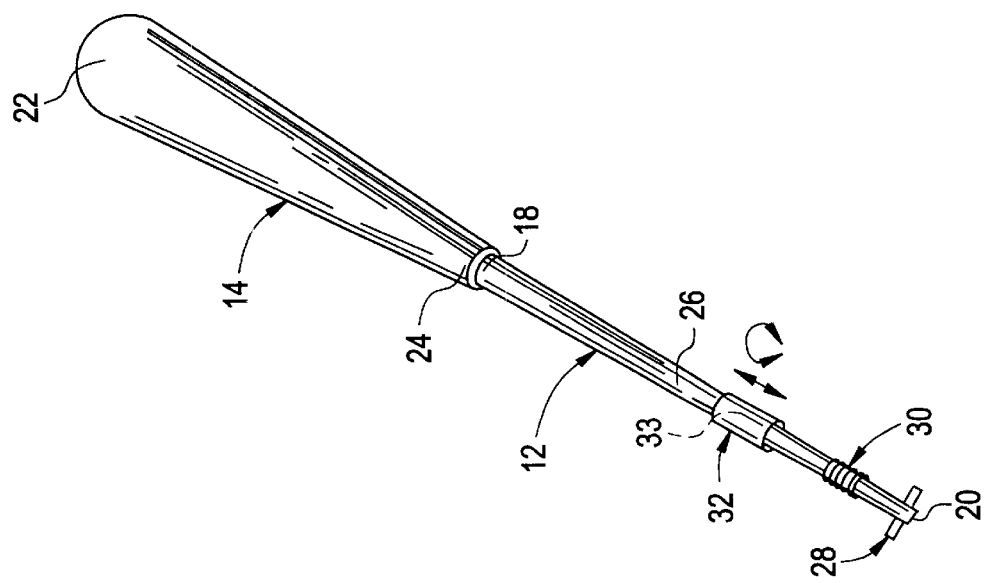
FIG. 2 is an enlarged diagrammatic perspective view of the area generally enclosed by the dotted curve indentified by ARROW 2 in FIG. 1 of the straight shank and the handle of the present invention.

The specific configuration of the shank 12 and the handle 14 can best be seen in FIG. 2 and 2A, which are, respectively, an enlarged diagrammatic perspective view of the area generally enclosed by the dotted curve indentified by ARROW 2 in FIG. 1 of the straight shank and the handle of the present invention, and a diagrammatic perspective view of the curved shank and the handle of the present invention, and as such, will be discussed with reference thereto.

The shank 12 is slender, elongated, made of stainless steel, can be either straight (FIG. 2) or curved (FIG. 2A), and has a proximal end 18 and a distal end 20, while the handle 14 is slender, enlongated, made of aluminum, and has a proximal end 22 that is free and a distal end 24 that is coincident with the proximal end 18 of the shank 12.

The shank 12 further has an intermediate point 26 that has a diameter and is disposed between the proximal end 18 thereof and the distal end 20 thereof, with the shank 12 tapering from the intermediate point 26 thereof to the distal end 20 thereof.

The shank 12 further has a pin 28 that is straight, extends perpendicularly therethrough and equidistantly from both sides thereof, and is disposed at the distal end 20 thereof.

The shank 12 further has male threads 30 that extend longitudinally along a portion thereof, and are disposed in proximity of the pin 28, towards the proximal end 18 of the shank 12.

The shank 12 further has a collar 32 that freely receives a portion thereof, has an internal diameter that is less than the diameter of the intermediate point 26 thereof so as to allow the collar 32 to be only longitudinally movable along the shank 12 between the male threads 30 and the intermediate point 26 of the shank 12 so as to limit travel of the collar 32 on the shank 12, and contains female threads 33 that extend longitudinally along a portion of the collar 32 and selectively engage the male threads 30 on the shank 12.

Figure 3:
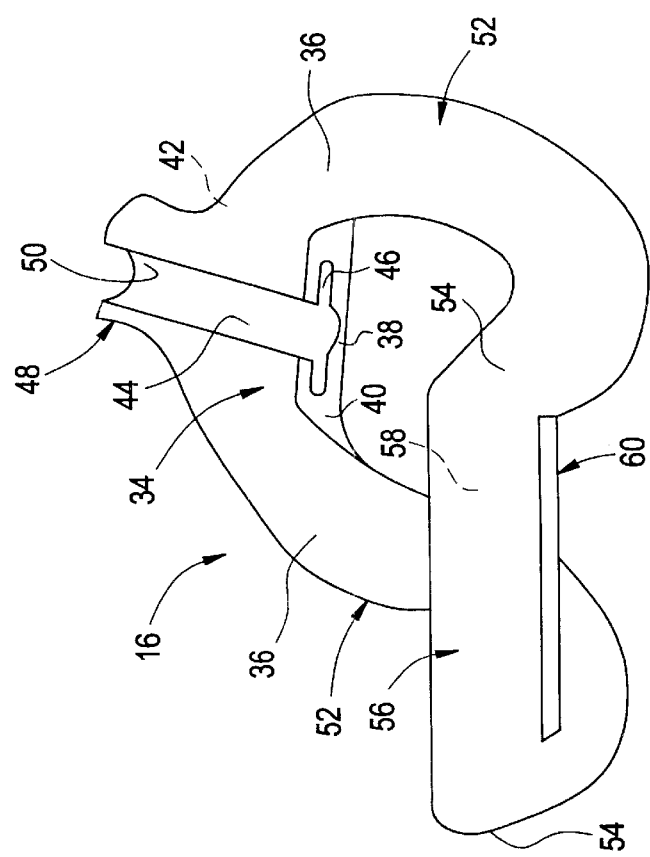
FIG. 3 is an enlarged diagrammatic perspective view of the area generally enclosed by the dotted curve identified by ARROW 3 in FIG. 1 of the cutting head of the present invention.
Figure 5A:
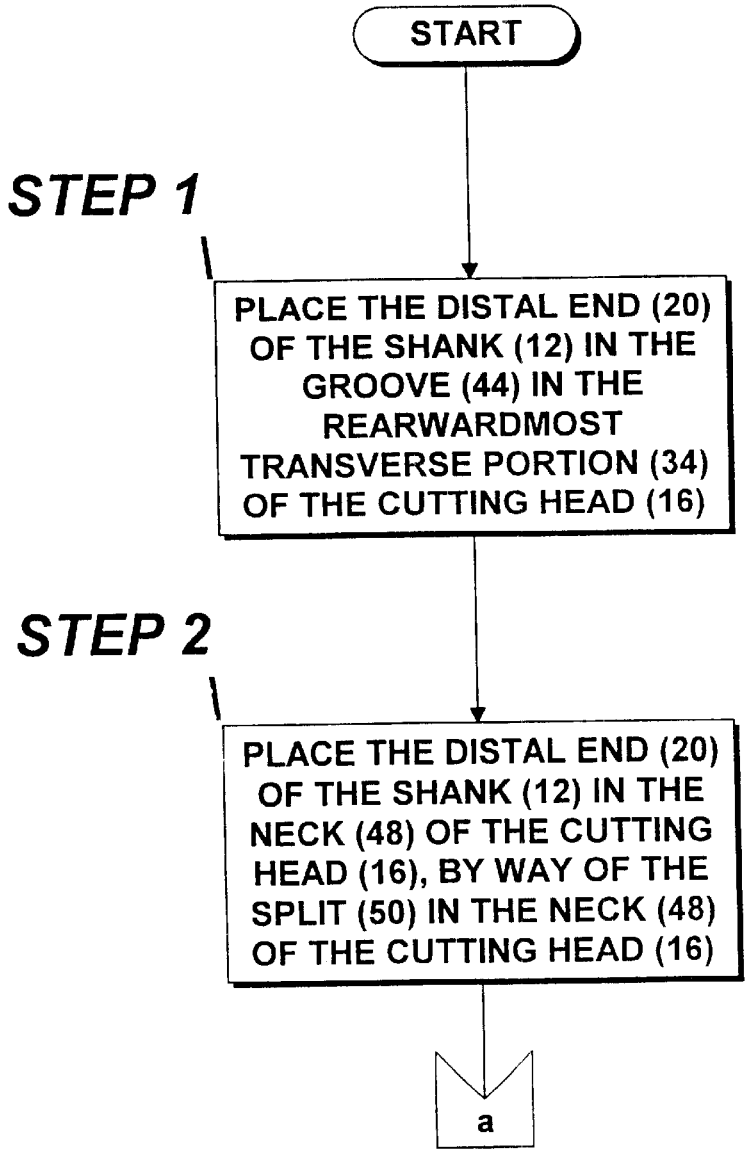
Figure 5B:
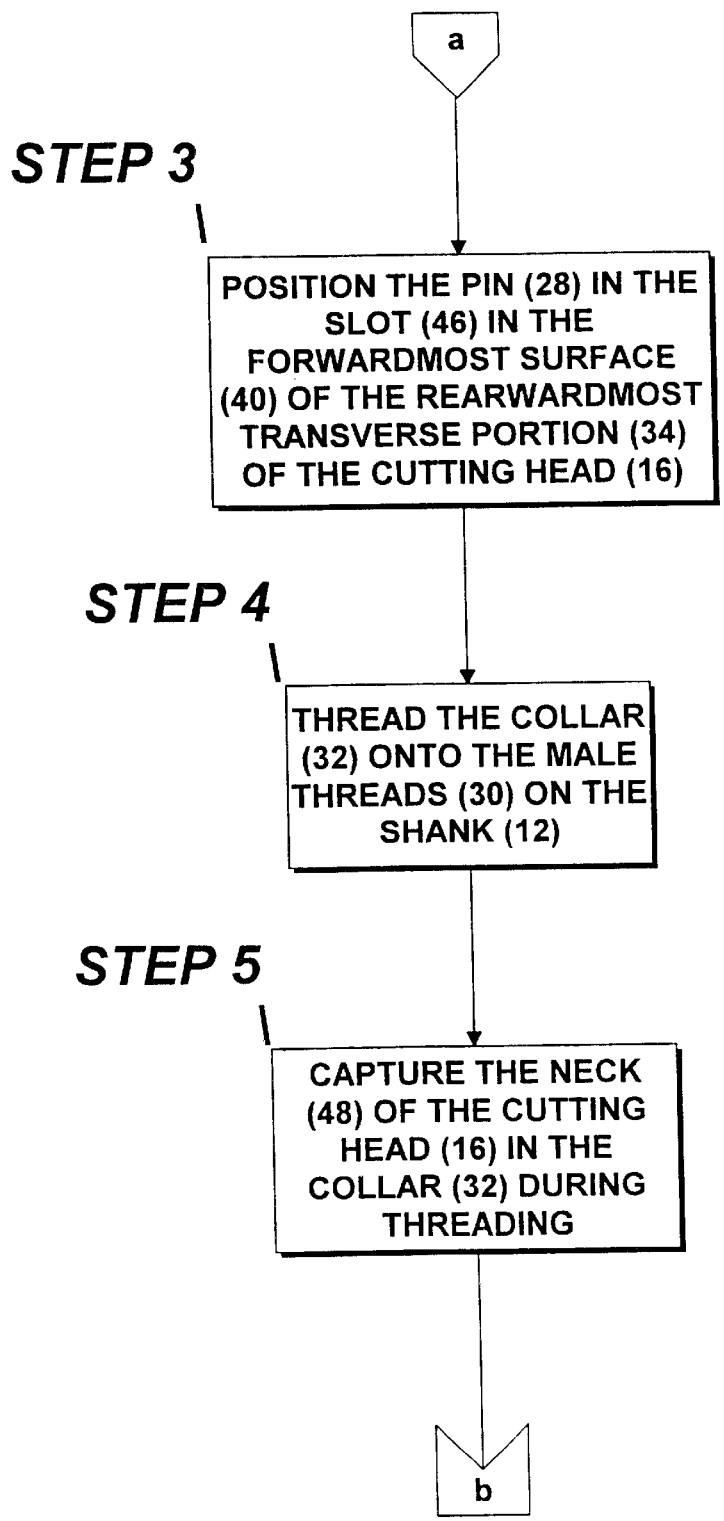

The specific configuration of the cutting head 16 can best be seen in FIG. 3, which is an enlarged diagrammatic perspective view of the area generally enclosed by the dotted curve identified by ARROW 3 in FIG. 1 of the cutting head of the present invention, and as such, will be discussed with reference thereto. Various sizes and/or types of the cutting heads can be color coded for ease of identification.

The cutting head 16 is made of molded plastic so as to be cost effective for disposal, is a loop that is continuous, and has a rearwardmost transverse portion 34 that is slender and has a pair of ends 36, a midpoint 38 that is midway between the pair of ends 36 thereof, a forwardmost surface 40, and a rearwardmost surface 42.

The rearwardmost transverse portion 34 of the cutting head 16 further has a groove 44 that extends perpendicularly therein, from the forwardmost surface 40 thereof to the rearwardmost surface 42 thereof, and is disposed at the midpoint 38 thereof.

The rearwardmost transverse portion 34 of the cutting head 16 further has a slot 46 that is disposed in the forwardmost surface 40 thereof and extends from short of one end 36 thereof to short of the other end 36 thereof, equidistantly from both sides of, and communicates with, the groove 44 therein.

The cutting head 16 further has a neck 48 that extends rearwardly and perpendicularly from the rearwardmost surface 42 of the rearwardmost transverse portion 34 thereof, is disposed at the midpoint 38 of the rearwardmost transverse portion 34 thereof, communicates with the groove 44, and has a split 50 that extends longitudinally and completely therealong and communicates with the groove 44.

The cutting head 16 further has a pair of legs 52 that are slender, parallel to each other, extend forwardly from the pair of ends 36 of the rearwardmost transverse portion 34 of the cutting head 16, respectively, to a pair of ends 54, respectively, and are perpendicular to the rearwardmost transverse portion 34 of the cutting head 16.

The pair of legs 52 of the cutting head 16 extend forwardly and upwardly in a concave configuration from the pair of ends 36 of the rearwardmost transverse portion 34 of the cutting head 16, respectively.

The cutting head 16 further has a forwardmost transverse portion 56 that is slender, extends from the end 54 of one leg 52 of the cutting head 16 to the end 54 of the other leg 52 of the cutting head 16, has a rearwardmost surface 58, is perpendicular to the pair of legs 52 of the cutting head 16, and is parallel to the rearwardmost transverse portion 34 of the cutting head 16.

The cutting head 16 further has a blade 60 that extends across the rearwardmost surface 58 of the forwardmost transverse portion 56 thereof.

The method of interchangeably retaining the cutting head 16 on the shank 12 can best be seen in FIGS. 4 and 5A–5C, which are, respectively, an exploded diagrammatic side elevational view taken generally in the direction of ARROW 4 in FIG. 1, and a flow chart of the method of interchangeably retaining the cutting head of the present invention shown in FIG. 3 on the shank of the present invention shown in FIG. 2, and as such, will be discussed with reference thereto.

STEP 1: Place the distal end 20 of the shank 12 in the groove 44 in the rearwardmost transverse portion 34 of the cutting head 16.

STEP 2: Place the distal end 20 of the shank 12 in the neck 48 of the cutting head 16, by way of the split 50 in the neck 48 of the cutting head 16.

STEP 3: Position the pin 28 in the slot 46 in the forwardmost surface 40 of the rearwardmost transverse portion 34 of the cutting head 16.

STEP 4: Thread the collar 32 onto the male threads 30 on the shank 12.

STEP 5: Capture the neck 48 of the cutting head 16 in the collar 32 during threading.

STEP 6: Abut the collar 32 against the rearwardmost transverse portion 34 of the cutting head 16 during threading so as to draw the pin 28 further into the slot 46 until the collar 32 can no longer rotate indicating that the pin 28 is fully seated in the slot 46 and thereby causing the rearwardmost transverse portion of the cutting head 16 to be captured between the pin 28 and the collar 32 and thereby interchangeably retaining the cutting head 16 on the shank 12.

It will be understood that each of the elements described above, or two or more together, may also find a useful application in other types of constructions differing from the types described above.

While the invention has been illustrated and described as embodied in an adenoid curette, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An adenoid curette, comprising:
  a) a shank;
  b) a handle; and
  c) a cutting head;
  wherein said handle extends coaxially from said shank; and
  wherein said cutting head is interchangeably retained on said shank so as to allow different cutting heads to be used for accommodating various characteristics of a patient and so as to allow said cutting head to be disposable and eliminate a need for sterilization and resharpening thereof;
  wherein said shank has a distal end;
  wherein said shank has a pin;
  wherein said pin is straight;
  wherein said pin extends perpendicularly through said shank;
  wherein said pin is disposed at said distal end of said shank; and
  wherein said pin extends equidistantly from both sides of said shank.

2. The curette as defined in claim 1, wherein said shank is slender;
  wherein said shank is elongated;
  wherein said handle is slender; and
  wherein said handle is elongated.

3. The curette as defined in claim 1, wherein said shank is made of stainless steel.

4. The curette as defined in claim 1, wherein said handle is made of aluminum.

5. The curette as defined in claim 1, wherein said shank is straight.

6. The curette as defined in claim 1, wherein said shank is curved.

7. The curette as defined in claim 1, wherein said handle has a
  distal end;
  wherein said shank has a proximal end;
  wherein said distal end of said handle is coincident with said proximal end of said shank;
  wherein said handle has a proximal end; and
  wherein said proximal end if said handle is free.

8. The curette as defined in claim 7, wherein said shank has an intermediate point;
  wherein said intermediate point of said shank is disposed between said proximal end of said shank and said distal end of said shank;
  wherein said intermediate point of said shank has a diameter; and
  wherein said shank tapers from said intermediate point thereof to said distal end thereof.

9. The curette as defined in claim 1, wherein said cutting head is made of molded plastic so as to be cost effective for disposal.

10. The curette as defined in claim 1, wherein said cutting head is a loop; and
  wherein said loop is continuous.

11. The curette as defined in claim 1, wherein said shank has male threads; wherein said male threads extend longitudinally along a portion of said shank; and wherein said male threads are disposed in proximity of said pin, towards said proximal end of said shank.

12. The curette as defined in claim 11, wherein said shank has a collar;
  wherein said collar has an internal diameter;
  wherein said collar contains female threads;
  wherein said female threads extend longitudinally along a portion of said collar;
  wherein said collar freely receives a portion of said shank;
  wherein said internal diameter of said collar is less than said diameter of said intermediate point of said shank so as to allow said collar to be only longitudinally movable along said shank between said male threads and said intermediate point of said shank so as to limit travel of said collar on said shank; and
  wherein said female threads in said collar selectively engage said male threads on said shank.

13. The curette as defined in claim 12, wherein said cutting head has a rearwardmost transverse portion;
  wherein said rearwardmost transverse portion of said cutting head is slender;
  wherein said rearwardmost transverse portion of said cutting head has a pair of ends;
  wherein said rearwardmost transverse portion of said cutting head has a midpoint;
  wherein said midpoint of said rearwardmost transverse portion of said cutting head is midway between said pair of ends of said rearwardmost transverse portion of said cutting head;
  wherein said rearwardmost transverse portion of said cutting head has a forwardmost surface;
  wherein said rearwardmost transverse portion of said cutting head has a rearwardmost surface;
  wherein said rearwardmost transverse portion of said cutting head has a groove;
  wherein said groove is disposed at said midpoint of said rearwardmost transverse portion of said cutting head;
  wherein said groove extends perpendicularly in said rearwardmost transverse portion of said cutting head; and
  wherein said groove extends from said forwardmost surface of said rearwardmost transverse portion of said cutting head to said rearwardmost surface of said rearwardmost transverse portion of said cutting head.

14. The curette as defined in claim 13, wherein said forwardmost surface of said rearwardmost transverse portion of said cutting head has a slot;
  wherein said slot extends from short of one end of said rearwardmost transverse portion of said cutting head to short of the other end of said rearwardmost transverse portion of said cutting head;
  wherein said slot extends equidistantly from both sides of said groove in said rearwardmost transverse portion of said cutting head; and wherein said slot communicates with said groove in said rearwardmost transverse portion of said cutting head.

15. The curette as defined in claim 14, wherein said cutting head has a neck;
wherein said neck is disposed at said midpoint of said rearwardmost transverse portion of said cutting head;
wherein said neck extends rearwardly from said rearwardmost surface of said rearwardmost transverse portion of said cutting head;
wherein said neck extends perpendicularly from said rearwardmost surface of said rearwardmost transverse portion of said cutting head; and
wherein said neck communicates with said groove in said rearwardmost transverse portion of said cutting head.

16. The curette as defined in claim 15, wherein said neck of said cutting head has a split;
wherein said split extends longitudinally along said neck of said cutting head;
wherein said split extends completely along said neck of said cutting head; and
wherein said split communicates with said groove in said rearwardmost transverse portion of said cutting head.

17. The curette as defined in claim 16, wherein said distal end of said shank is received in said groove in said rearwardmost transverse portion of said cutting head and in said neck of said cutting head, by way of said split in said neck of said cutting head;
wherein said pin is received in said slot in said forwardmost surface of said rearwardmost transverse portion of said cutting head; and
wherein said collar threads onto said male threads on said shank, captures said neck of said cutting head, and abuts against said rearwardmost transverse portion of said cutting head during threading so as to force said pin further into said slot until said collar can no longer rotate indicating that said pin is fully seated in said slot, and in doing so, said rearwardmost transverse portion of said cutting head is captured between said pin and said collar and said cutting head is interchangeably retained on said shank.

18. The curette as defined in claim 13, wherein said cutting head has a pair of legs;
wherein said pair of legs of said cutting head are slender;
wherein said pair of legs of said cutting head are parallel to each other;
wherein said pair of legs of said cutting head extend forwardly from said pair of ends of said rearwardmost transverse portion of said cutting head, respectively, to a pair of ends, respectively;
wherein said pair of legs of said cutting head extend forwardly and upwardly in a concave configuration from said pair of ends of said rearwardmost transverse portion of said cutting head, respectively; and
wherein said pair of legs of said cutting head are perpendicular to said rearwardmost transverse portion of said cutting head.

19. The curette as defined in claim 18, wherein said cutting head has a forwardmost transverse portion;
wherein said forwardmost transverse portion of said cutting head is slender;
wherein said forwardmost transverse portion of said cutting head has a rearwardmost surface;
wherein said forwardmost transverse portion of said cutting head extends from said end of one leg of said cutting head to said end of the other leg of said cutting head;
wherein said forwardmost transverse portion of said cutting head is perpendicular to said pair of legs of said cutting head; and
wherein said forwardmost transverse portion of said cutting head is parallel to said rearwardmost transverse portion of said cutting head.

20. The curette as defined in claim 19, wherein said cutting head has a blade; and
wherein said blade extends across said rearwardmost surface of said forwardmost transverse portion of said cutting head.

21. A method of interchangeably retaining a cutting head on a shank of an adenoid curette, comprising the steps of:
a) placing a distal end of said shank in a groove in a rearwardmost transverse portion of said cutting head;
b) placing said distal end of said shank in a neck of said cutting head, by way of a split in said neck of said cutting head;
c) positioning a pin of said shank in a slot in a forwardmost surface of said rearwardmost transverse portion of said cutting head;
d) threading a collar of said shank onto male threads on said shank;
e) capturing said neck of said cutting head in said collar during threading; and
f) abutting said collar against said rearwardmost transverse portion of said cutting head during threading so as to draw said pin further into said slot until said collar can no longer rotate indicating that said pin is fully seated in said slot and thereby causing said rearwardmost transverse portion of said cutting head to be captured between said pin and said collar and thereby interchangeably retaining said cutting head on said shank.

22. An adenoid curette, comprising:
a) a shank;
b) a handle; and
c) a cutting head;
wherein said handle extends coaxially from said shank;
wherein said cutting head is interchangeably retained on said shank so as to allow different cutting heads to be used for accommodating various characteristics of a patient and so as to allow said cutting head to be disposable and eliminate a need for sterilization and resharpening thereof;
wherein said shank has a distal end;
wherein said shank has a proximal end;
wherein said handle has a distal end;
wherein said distal end of said handle is coincident with said proximal end of said shank;
wherein said handle has a proximal end; and
wherein said proximal end of said handle is free.

23. An adenoid curette, comprising:
a) a shank;
b) a handle; and
c) a cutting head;
wherein said handle extends coaxially from said shank;
wherein said cutting head is interchangeably retained on said shank so as to allow different cutting heads to be used for accommodating various characteristics of a patient and so as to allow said cutting head to be disposable and eliminate a need for sterilization and resharpening thereof;
wherein said cutting head is a loop; and
wherein said loop is continuous.

* * * * *